United States Patent [19]
Alicot et al.

[11] 4,192,804
[45] Mar. 11, 1980

[54] PROCESS FOR THE PURIFICATION OF MERCAPTOBENZOTHIAZOLE

[75] Inventors: Michel J. C. Alicot; René H. P. Rhode, both of Lannemezan; Adrien P. N. Tignol, Montrejeau, all of France

[73] Assignee: Produits Chimiques Ugine Kuhlmann Service Propriete Industrielle, Paris, France

[21] Appl. No.: 922,417

[22] Filed: Jul. 6, 1978

[30] Foreign Application Priority Data

Jul. 12, 1977 [FR] France .................. 77 21437

[51] Int. Cl.² ........................... C07D 277/72
[52] U.S. Cl. ........................................... 548/177

[58] Field of Search ........................... 260/306

[56] References Cited

U.S. PATENT DOCUMENTS

| 3,030,373 | 4/1962 | Szlatinay | 260/306 |
| 3,904,638 | 9/1975 | Sagawa et al. | 260/306 |

Primary Examiner—Nicholas S. Rizzo
Attorney, Agent, or Firm—Beveridge, DeGrandi, Kline & Lunsford

[57] ABSTRACT

Process for the purification of mercaptobenzothiazole prepared according to known processes, characterized in that the crude product is treated with carbon tetrachloride or with 1,1,2,2-tetrachloroethylene.

7 Claims, No Drawings

PROCESS FOR THE PURIFICATION OF MERCAPTOBENZOTHIAZOLE

BACKGROUND OF THE INVENTION

1. Field of the Invention

The present invention relates to the purification of mercaptobenzothiazole and particularly to the purification of mercaptobenzothiazole prepared according to known processes.

2. Description of the Prior Art

Mercaptobenzothiazole is known in the elastomer conversion industry for its utilization as a vulcanization accelerator. It is likewise an important raw material in the synthesis of improved vulcanization accelerators which are adapted to the particular problems posed by the manufacture of articles as different as, for example, pneumatic tires, electric cables, shoe soles, and insulation joints. It also enters widely into the synthesis of plant protection compounds.

Most of the known processes of manufacture make use of the reaction, in appropriate proportions and at high temperature and high pressure, of aniline, sulfur, and carbon disulfide. Others make use of the reaction of thiocarbanilide, carbon disulfide and sulfur (U.S. Pat. No. 1,712,968, issued May 14, 1929), or of the reaction of orthochloronitrobenzene, hydrogen sulfide or an alkaline sulfide, and carbon disulfide (U.S. Pat. No. 1,960,205, issued May 22, 1934; Polish Pat. No. 86,988, issued Dec. 15, 1976); or to the reaction of benzothiazole and sulfur (German Pat. No. 2,551,060 issued May 6, 1976). The reaction product obtained under such conditions can never be utilized directly as it is. It contains, in fact, raw materials which have not reacted, for example, aniline, etc.; and by-products and intermediates such as benzothiazole or anilinobenzothiazole. A careful purification of the crude reaction product is necessary.

Numerous purification processes have been proposed in the past. These processes fundamentally make use of two techniques which differ mainly in the concentrations, order of use, and nature of the recommended reagents, and in the temperatures of treatment.

The basic steps of the principle of the first technique are as follows:

1. Solution of the reaction product in an alkaline medium (ammonium hydroxide, sodium hydroxide, lime), optionally preceded by a treatment in a mineral acid medium;
2. Separation of the insoluble impurities by filtration;
3. Separation of the soluble impurities after they have been made insoluble by oxidation and/or extraction by means of a solvent; and
4. Precipitation of the mercaptobenzothiazole by the action of a mineral acid.

U.S. Pat. Nos. 1,631,871; 2,658,864; 2,730,528; and 3,818,025 and French Pat. No. 2,135,807 illustrate the application of the whole, or a part, of such a process.

In the second technique, the impurities are extracted by treatment of the reaction product with carbon disulfide or an emulsion of carbon disulfide and water.

U.S. Pat. Nos. 2,090,233; 3,030,373; and 3,031,073 illustrate this embodiment.

Although they are industrially exploited at present, these processes are not satisfactory and each present one or more of the following disadvantages:

1. Difficult recovery of the unreacted raw materials, which are economically very important to recycle (aniline in particular);
2. Necessity of operation at low concentrations to favor the precipitation of impurities, with the consequential use of apparatus of large dimensions;
3. Losses, by chemical degradation, of mercaptobenzothiazole during the course of the oxidation reactions intended to render the impurities insoluble in an alkaline medium;
4. Losses, by solution in the carbon disulfide, of mercaptobenzothiazole, or inevitable recycling of part of the impurities if the quantity of carbon disulfide is limited; and
5. Finally, and this is probably the major disadvantage of these processes, the necessity of having to treat large volumes of aqueous effluents, containing heavy pollutant loads, before their release. These treatments are difficult and costly. The oxidation processes generally applied do not lead to the desired simple molecules of nitrogen, carbon dioxide and sulfur dioxide, but to an unacceptable level of soluble molecules which are not degraded by a complementary biological treatment, heavily adding to the cost per unit of production.

SUMMARY OF THE INVENTION

It has now been found that mercaptobenzothiazole can be obtained in a high yield and in a highly pure state, starting from the crude product of known processes, by means of a simplified technology. Thanks to this process, the intermediate products and unreacted raw materials can easily be recycled, and the by-products can be separated without difficulty. In addition, because water is not utilized, the problems of effluent treatment are removed.

The process according to the invention, for the purification of mercaptobenzothiazole, comprises treating the crude product obtained according to known processes with carbon tetrachloride or with 1,1,2,2-tetrachloroethylene ($CL_2$—C=C—$Cl_2$) with or without prior distillation of the volatile products.

DESCRIPTION OF THE PREFERRED EMBODIMENTS

When the process of purification is applied to the crude product separated from volatile products (such as aniline and benzothiazole, which are recyclable after recovery), the separation of the volatile products can be carried out in a first phase by a distillation over a large temperature range (100° to 300° C.).

Because of the risks of thermal decomposition of the mercaptobenzothiazole, it is desirable that this temperature is below 220° C., the preferred range being from 100° to 150° C. A thinfilm scraper evaporator which permits the solid product to be recovered in the form of a powder is advantageously utilized. The vacuum which it is necessary to maintain in the apparatus is a function of the temperature choses: it generally ranges between 10 and 200 millimiters of mercury.

In a second phase, the crude mercaptobenzothiazole to be purified, obtained after distillation, is suspended in carbon tetrachloride or 1,1,2,2-tetrachloroethylene.

When the process of purification is applied without prior separation of the volatile products, the crude reaction product is directly suspended in carbon tetrachlorie or 1,1,2,2-tetrachloroethylene. The recovery of the products which can be recycled is effected in this embodiment by distillation of the solvent phase after separation of the insolubilized purified mercaptobenzothiazole.

In all embodiments, for economic reasons, it is preferable to limit the concentration of the solid product in suspension in the solvent to an amount between 200 and 400 grams per liter. The finer the state of subdivision of the product to be purified, the easier is the solution and removal of the impurities. Any known means permit this condition to be easily attained.

The treatment according to the present invention can be carried out within a large range of temperatures, i.e., from 0° to 77° C., the boiling point of carbon tetrachloride at a pressure of 760 mm of mercury, preferably in the range of 10° to 50° C., and from 0° to 121° C., the boiling point of 1,1,2,2-tetrachloroethylene at a pressure of 760 mm of mercury, preferably in the range of 10° to 80° C.

Carrying out the treatment at temperatures lower or higher than the above-mentioned preferred ranges does not detract from the invention, but is without any particular interest and can needlessly complicate the equipment.

The final recovery of the mercaptobenzothiazole is effected by any known means of filtration and drying. The filtrate is subjected to a distillation so as to recover the carbon tetrachloride or the 1,1,2,2-tetrachloroethylene and to separate the products to be recycled, either wholly or in part.

The following examples illustrate the invention without limiting it. In the examples and throughout the specification and claims, all parts and percentages are by weight unless otherwise specified.

EXAMPLE 1

At a temperature of 180° C. 1000 grams of the reaction product of aniline, carbon disulfide and sulfur is taken from the exit of a synthesis reactor, after removal of hydrogen sulfide gas, and has the following composition:

| Mercaptobenzothiazole | 83.5% |
| --- | --- |
| Aniline | 3.2% |
| Benzothiazole | 2.0% |
| Various by-products | 11.3% |

This product is introduced into a scraper evaporator within which are established a temperature of 130° C. and a reduced pressure of 15 mm of mercury. The volatiles distill off and 54 grams of a pale yellow oil are collected by condensation, with a titre of 57.3% aniline and 35.2% benzothiazole. The solid product extracted from the evaporator is crushed and suspended in 2,300 ml of carbon tetrachloride at 25° C. After an hour of agitation, the suspension is filtered, washed twice with 300 ml each time of carbon tetrachloride, drained and dried.

There are obtained 836.5 grams of a pale yellow product, with a titre of 99% of mercaptobenzothiazole and an uncorrected melting point of 177°-180° C. The yield of the purification is 99.2%.

The fraction containing the aniline and the benzothizaole can be recycled into the synthesis reactor without further treatment. The solution of carbon tetrachloride containing the byproducts is distilled in order to recover the solvent which can be recycled. A non-distillable fraction of 109 grams in weight is recovered; it can be recycled into the manufacture of mercaptobenzothiazole.

The mercaptobenzothiazole which is subjected to purification can be the crude product obtained according to any of the known processes for its preparation; among others, that of U.S. Pat. No. 1,631,871 may be cited.

EXAMPLE 2

Example 1 is repeated with the exception that 1,1,2,2-tetrachloroethylene was used instead of carbon tetrachloride. The results are identical. The mercaptobenzothiazole subjected to purification may be the crude product obtained from any of the known processes for its preparation, without any preference.

EXAMPLE 3

At the exit of a synthesis reactor, at 200° C., there are collected 1,000 grams of the reaction product of aniline, sulfur and carbon disulfide, having the following composition:

| Mercaptobenzothiazole | 83.5% |
| --- | --- |
| Aniline | 3.2% |
| Benzothiazole | 2.0% |
| Various by-products | 11.3% |

This product is introduced, with agitation, during about thirty minutes, into 2,000 ml of 1,1,2,2-tetrachloroethylene kept cooled to 20° to 25° C. After one hour of agitation, the suspension of mercaptobenzothiazole is filtered off, washed with two or three 200-ml portions of 1,1,2,2-tetrachloroethylene, drained and dried. There are obtained grams of product having a pale yellow color, with a titer of 98.5% of mercaptobenzothiazole of uncorrected melting point 177°-180° C. The yield of the purification is 97.5%.

From the solvent phase recovered by the filtration, there are obtained by distillation 50 grams of a mixture of aniline and benzothiazole, which can be recycled.

EXAMPLE 4

Example 3 is repeated, with the exception that the 1,1,2,2-tetrachloroethylene is replaced by carbon tetrachloride. The results are identical.

What is claimed is:

1. A process for the purification of mercaptobenzothiazole prepared according to known processes which comprises treating the crude product in the absence of water with carbon tetrachloride or with 1,1,2,2-tetrachloroethylene.

2. The process as claimed in claim 1 in which the crude product is treated with carbon tetrachloride or with 1,1,2,2-tetrachloroethylene without prior separation of volatile materials therefrom.

3. The process as claimed in claim 1 in which the crude product is treated with carbon tetrachloride or with 1,1,2,2-tetrachloroethylene after prior separation of the volatile materials by distillation under reduced pressure.

4. The process as claimed in claim 3 in which the distillation is carried out at a temperature below 220° C. and under a pressure of 10 to 200 millimeters of mercury.

5. The process as claimed in claim 1 wherein the crude product is suspended in the carbon tetrachloride or in the 1,1,2,2-tetrachloroethylene at a temperature equal to, or lower than, the boiling point of the solvent.

6. The process as claimed in claim 1 wherein the purified mercaptobenzothiazole, rendered insoluble in carbon tetrachloride or in 1,1,2,2-tetrachloroethylene, is separated by physical means.

7. The process as claimed in claim 1 wherein the solvent phase obtained after separation of the purified mercaptobenzothiazole is distilled so as to recover the carbon tetrachloride or the 1,1,2,2-tetrachloroethylene.

* * * * *